US00PP30313P2

(12) United States Plant Patent
Van Swieten

(10) Patent No.: US PP30,313 P2
(45) Date of Patent: Mar. 26, 2019

(54) ***PHALAENOPSIS* ORCHID PLANT NAMED 'PHALFUEOZ'**

(50) Latin Name: ***Phalaenopsis* hybrid**
Varietal Denomination: PHALFUEOZ

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/732,860

(22) Filed: Jan. 5, 2018

(51) Int. Cl.
*A01H 5/02* (2018.01)

(52) U.S. Cl.
USPC ..... Plt./311

(58) Field of Classification Search
USPC ..... Plt./311
CPC ..... A01H 5/02; A01H 6/62
See application file for complete search history.

*Primary Examiner* — Keith O. Robinson
(74) *Attorney, Agent, or Firm* — Jondle & Associates, P.C.

(57) ABSTRACT

A new and distinct variety of *Phalaenopsis* plant named 'PHALFUEOZ', particularly characterized by having small, dark red flowers with a white edge, 2 to 3 peduncles that are short and sturdy, leaves that are oblong, and is propagated by meristem tissue culture, is disclosed.

3 Drawing Sheets

Genus and species: *Phalaenopsis* hybrid.
Variety denomination: 'PHALFUEOZ'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFUEOZ'.

The new *Phalaenopsis* plant is a product of a planned breeding program conducted by the inventor in Bleiswijk, The Netherlands. The objective of this breeding program was to create a new *Phalaenopsis* plant with numerous attractive and unique small, dark red flowers with a white edge, suitable for potted plant production.

The new *Phalaenopsis* plant 'PHALFUEOZ' is a result of cross-pollination made by the inventor in March 2008 in Bleiswijk, The Netherlands of the proprietary female, or seed parent, *Phalaenopsis* hybrid '20413-03' (unpatented) with the proprietary male, or pollen parent, *Phalaenopsis* hybrid '01-2077' (unpatented).

The new *Phalaenopsis* was selected by the inventor as a single plant within the progeny of the stated cross-pollination in a controlled greenhouse in Bleiswijk, The Netherlands in April 2011. Asexual reproduction of the new *Phalaenopsis* plant by meristem tissue culture since 2014 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 24, 2017. 'PHALFUEOZ' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALFUEOZ' as a new and distinct variety of *Phalaenopsis* plant.

1) Small, dark red flowers with a white edge;
2) 2 to 3 peduncles;
3) Peduncle is short and sturdy; and
4) Shape of the leaf is oblong.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs were taken in a greenhouse in Bleiswijk, The Netherlands, from 30- to 35-week old plants in October 2017. Colors in the photographs may differ from the color values cited in the detailed botanical description, which accurately describe the actual colors of the new variety.

DESCRIPTION OF THE NEW VARIETY

Figure 1:
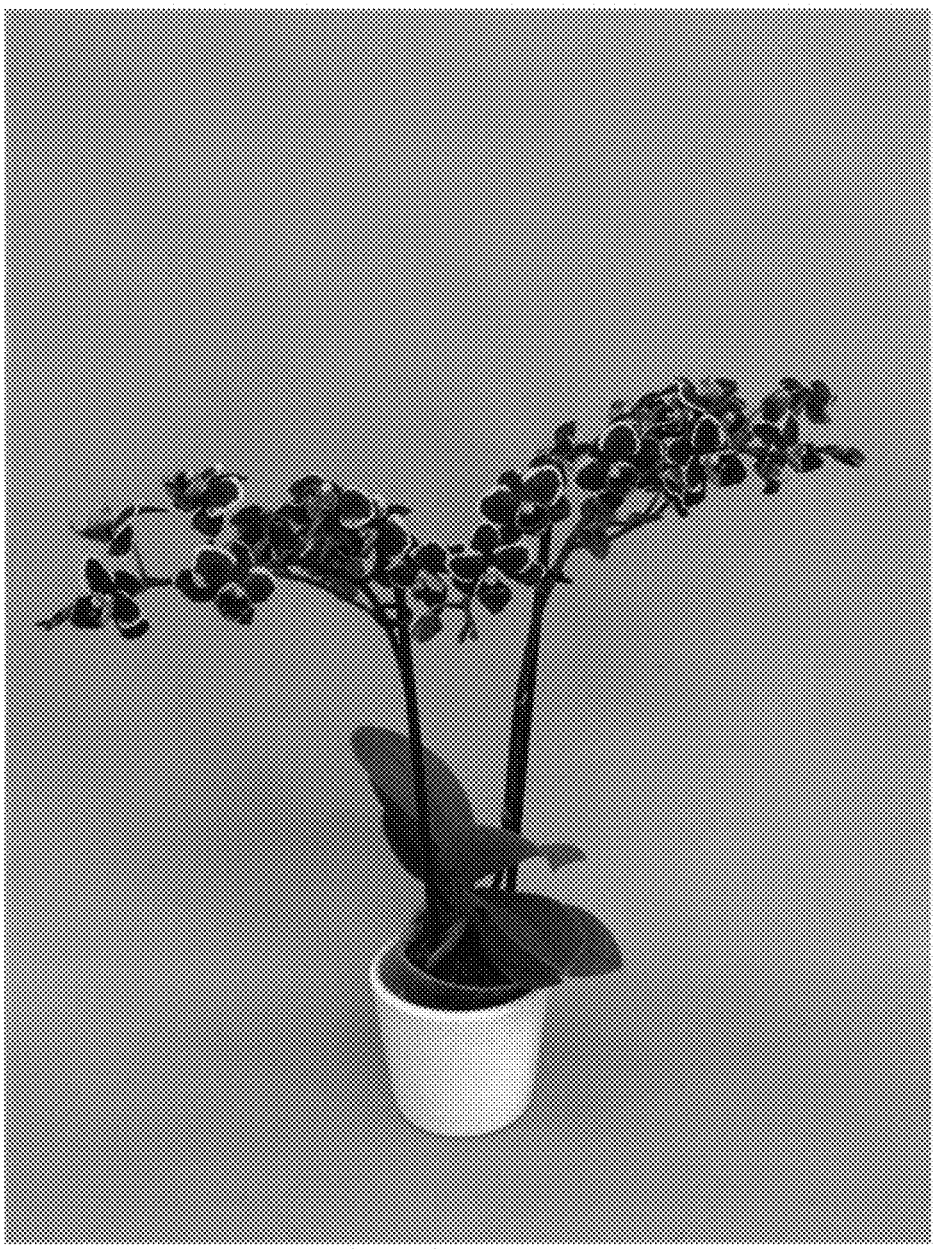
FIG. 1 shows the overall plant habit, including blooms, buds and foliage of 'PHALFUEOZ'.
Figure 2:
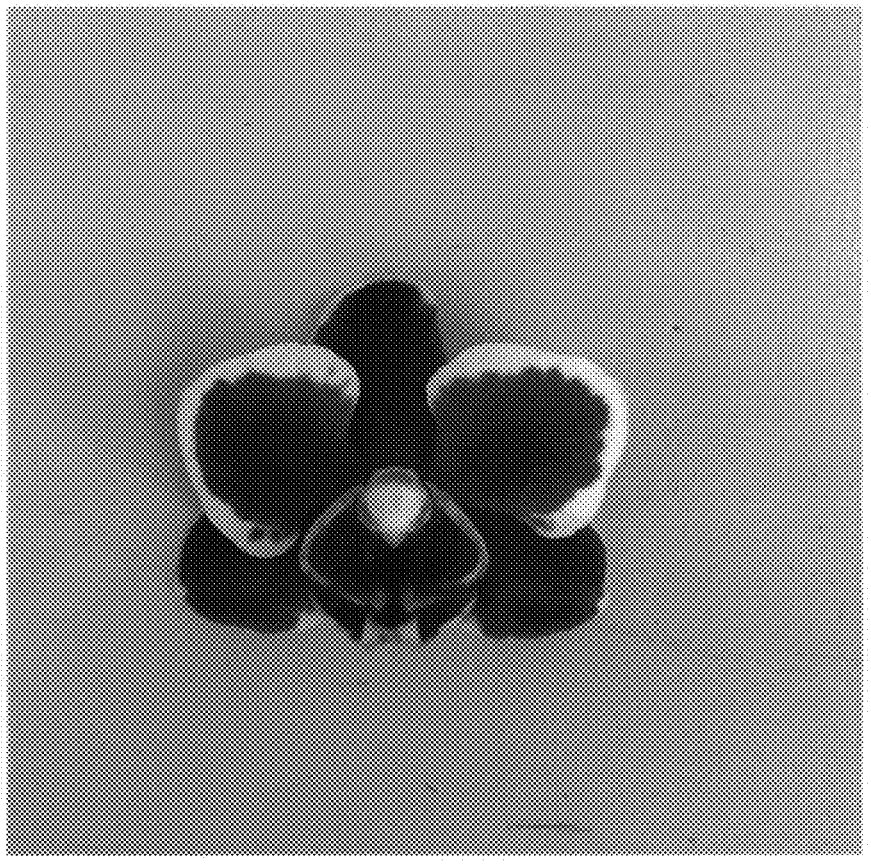
FIG. 2 shows a close-up of a flower of 'PHALFUEOZ'.
Figure 3:
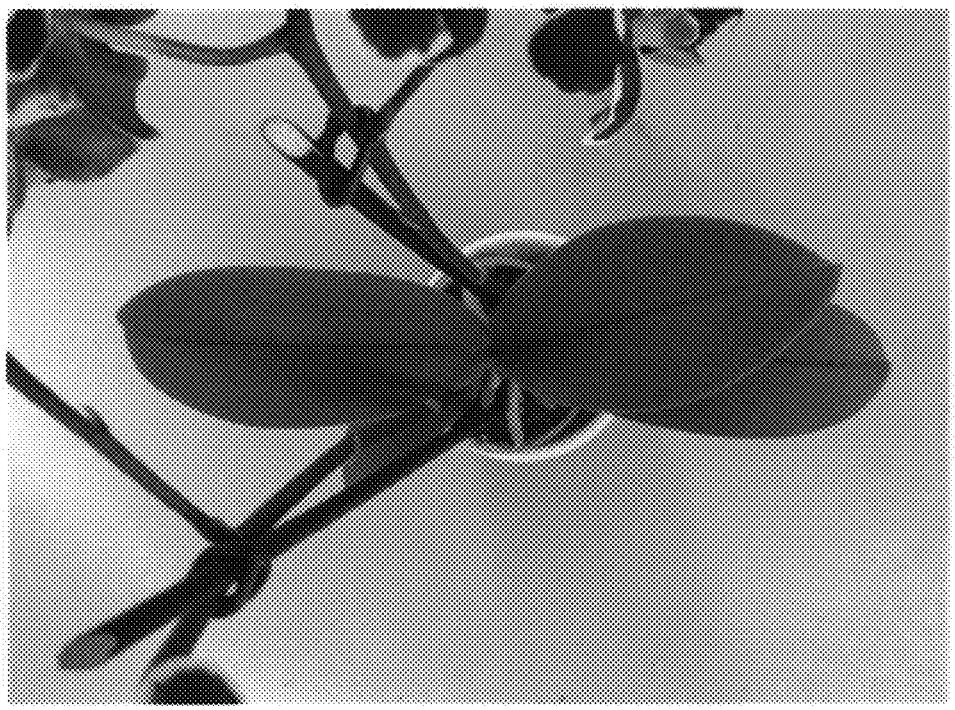
FIG. 3 shows an overhead view of the leaves of 'PHALFUEOZ'.

The following detailed description sets forth the distinctive characteristics of. 'PHALFUEOZ'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-

6000 lux natural light in a greenhouse in Bleiswijk, The Netherlands. Observations and measurements were made in October 2017 on 30- to 35-week old plants which were planted from a nursery tray in 6 centimeter (diameter) pots and grown in a greenhouse between 27° C. to 29° C. for 20 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALFUEOZ'.

Parentage:

*Female parent*.—*Phalaenopsis* cultivar '20413-03' (unpatented).

*Male parent*.—*Phalaenopsis* cultivar '01-2077' (unpatented).

Propagation:

*Type*.—Meristem tissue culture.

Roots:

*Root description*.—Greyed-green colored roots (RHS 190B/C) with branching lateral roots having light green colored root tips (RHS 145C).

Plant:

*Commercial crop time to flowering*.—Following asexual propagation (in-vitro), the plants are transplanted directly into a 6 cm pot; the plants are finished after 48 to 50 weeks.

*Growth habit of peduncle*.—Standard, green leaves, panicle.

*Height (from soil level to top of inflorescence)*.—Approximately 25.0 cm to 30.0 cm.

*Width (measured from leaf tips)*.—About 18.0 cm to 19.0 cm.

*Vigor*.—Moderate.

Leaves:

*Mature leaves*.—Quantity per plant: 7 to 9 leaves are produced before flowering. Length (fully expanded): 9.0 cm to 10.0 cm. Width: 4.0 cm to 4.5 cm. Shape: Oblong. Base shape: Moderately elongated. Apex: A cute unequal. Leaf blade angle with the petiole (measured from the horizontal position): Between 25 degrees and 40 degrees. Leaf margin: Entire. Color: Upper surface: RHS 146A. Lower surface: RHS 146B. Texture: Rough. Thickness: 1.5 mm to 1.7 mm. Venation: Pattern: Parallel. Color of the midvein: Upper surface: RHS 146A. Lower surface: RHS 146B.

Peduncle:

*Quantity per plant*.—2 to 3.

*Number of flowers per peduncle*.—13 to 23.

*Length*.—25.0 cm to 30.0 cm.

*Diameter*.—3.3 mm to 3.8 mm.

*Strength*.—Moderate.

*Aspect*.—Upright to slightly pendant.

*Texture*.—Smooth.

*Color*.—Mix of brown (RHS N200A) and green (RHS 146B).

*Internode length*.—2.5 cm to 4.5 cm.

*Callosities*.—None.

Inflorescence description:

*Appearance*.—Upright to slightly pendant, panicle inflorescence with bilaterally symmetrical flowers that open in succession beginning with the lowermost flower.

*Inflorescence size*.—Height (from base to tip): 130.0 mm to 160.0 mm.

*Flowering time*.—First flowers can be expected 8 to 9 months after planting in a 6 cm (diameter) pot.

*Flower*.—Height: 27.0 mm to 32.0 mm. Diameter: 30.0 mm to 35.0 mm. Depth of lip: 10.0 mm to 12.0 mm.

*Flower longevity*.—On the plant: 8 to 13 weeks.

*Fragrance*.—Absent.

*Flower bud*.—Average size: Small. Length: 9.0 mm to 11.0 mm. Width: 8.0 mm to 10.0 mm. Shape: Egg shaped. Color: Red-purple (RHS N77A/C) and light green (RHS 145D).

*Petals*.—Arrangement: Open/free. Shape: Semi-circular. Apex: Obtuse asymmetric. Margin: Slightly undulated. Length (from base to tip): 13.0 mm to 15.0 mm. Width: 14.0 mm to 16.0 mm. Color (when fully opened): Upper surface: Basic color: Dark red (RHS 187A/B). Over color: White edge (RHS NN155C). Lower surface: Basic color: Purple (RHS N78C) region in the middle. Over color: Few dark red-purple (RHS N79C) spots; white edge (RHS NN155C).

*Dorsal sepal*.—Shape: Elliptic. Apex: Rounded symmetric. Margin: Entire. Length (from base to tip): 15.0 mm to 17.0 mm. Width: 9.0 mm to 11.0 mm. Color (when fully opened): Upper surface: Basic color: Dark red (RHS 187A/B). Over color: Very small light purple (RHS 76B) edge. Lower surface: Basic color: Diluting dark red-purple (RHS N79B/C). Over color: Very small light purple (RHS 76B) edge.

*Lateral sepals*.—Shape: Ovate. Apex: Obtuse asymmetric. Margin: Entire. Length (from base to tip): 16.0 mm to 18.0 mm. Width: 11.0 mm to 13.0 mm. Color (when fully opened): Upper surface: Basic color: Dark red (RHS 187A/B). Over color: Very small light purple (RHS 76B) edge. Lower surface: Basic color: Diluting dark red-purple (RHS N79B/C). Over color: Light purple (RHS 76B) edge and slightly green (RHS 146D) at the base.

*Labellum (lip)*.—Whiskers: Present. Length of whiskers: 0.0 mm to 1.0 mm. Color of whiskers: Dark purple red (RHS N79A). Pubescence on the lip: Absent.

*Lateral lobe*.—Margin: Slightly undulated. Length: 10.0 mm to 12.0 mm. Width: 8.0 mm to 10.0 mm. Color: Dark red (RHS 187A/B) at the base; white (RHS NN155C) and yellow (RHS 8B) toward margin.

*Apical lobe*.—Shape: Circular. Margin: Entire. Length: 12.0 mm to 14.0 mm. Width: 11.0 mm to 13.0 mm. Color: Yellow (RHS 14A) at the base; dark red (RHS 187A/B) spots.

*Callus*.—Average size: Small. Height: 3.0 mm to 4.0 mm. Length: 3.0 mm to 4.0 mm. Width: 1.0 mm to 2.0 mm. Color: Dark red (RHS 187A) and yellow (RHS 14B) on sides.

Reproductive organs:

*Column*.—Length: 7.0 mm to 9.0 mm. Diameter: 4.3 mm to 4.8 mm. Color: White (RHS NN155C) at the base; purple (RHS N78B) toward the tip.

*Pollinia*.—Quantity: 2. Diameter: 0.8 mm to 1.0 mm. Color: Orange (RHS 25A).

*Ovary*.—Length: 6.0 mm to 8.0 mm. Diameter: 1.6 mm to 1.8 mm.

*Pedicel*.—Length: 19.0 mm to 21.0 mm. Diameter: 1.8 mm to 2.0 mm. Color: Dark red-purple (RHS N77A/B) at the base; light purple (RHS 75D and 76C) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALFUEOZ' differs from female parent plant '20413-03' (unpatented) in that 'PHALFUEOZ' has dark red flowers, a dark red callus and dark purple-red whiskers, whereas '20413-03' has purple flowers, a yellow callus and yellow whiskers. Additionally, 'PHALFUEOZ' has smaller flowers than '20413-03'.

'PHALFUEOZ' differs from male parent plant '01-2077' (unpatented) in that 'PHALFUEOZ' has dark red flowers with an edge pattern and dark purple-red whiskers, whereas '01-2077' has white flowers with a flecked pattern and red-purple whiskers. Additionally, 'PHALFUEOZ' has smaller flowers than '01-2077'.

'PHALFUEOZ' is most similar to the commercial *Phalaenopsis* plants named 'PHALDIMAN' (unpatented) and 'PHALFEQBIN' (U.S. Plant patent application Ser. No. 15/530,070). 'PHALFUEOZ' differs from the commercial variety 'PHALDIMAN' in that 'PHALFUEOZ' has flowers with a white edge pattern, a circular apical lobe and whiskers, whereas 'PHALDIMAN' has flowers with a light yellow edge pattern with some spots, an ovate apical lobe and no whiskers. Additionally, 'PHALFUEOZ' has smaller flowers than 'PHALDIMAN'.

'PHALFUEOZ' differs from the commercial variety 'PHALFEQBIN' in that 'PHALFUEOZ' has flowers with a white edge pattern and a circular apical lobe, whereas 'PHALFEQBIN' has flowers with a dark purple-red spotted pattern and a triangular apical lobe. Additionally, 'PHALFUEOZ' has smaller flowers and shorter whiskers than 'PHALFEQBIN'.

I claim:

1. A new and distinct variety of *Phalaenopsis* plant named 'PHALFUEOZ', substantially as described and illustrated herein.

* * * * *